(12) United States Patent
Bertagnoli et al.

(10) Patent No.: US 7,763,024 B2
(45) Date of Patent: Jul. 27, 2010

(54) ADJUSTABLE CUTTING OF CUTOUT IN VERTEBRAL BONE

(75) Inventors: Rudi Bertagnoli, Vienna (AT); David Gerber, West Chester, PA (US)

(73) Assignee: Spine Solutions, Inc., West Chester, PA (US)

( * ) Notice: Subject to any disclaimer, the term of this patent is extended or adjusted under 35 U.S.C. 154(b) by 1590 days.

(21) Appl. No.: 10/947,661

(22) Filed: Sep. 23, 2004

(65) Prior Publication Data

US 2006/0064100 A1    Mar. 23, 2006

(51) Int. Cl.
A61B 17/00    (2006.01)
(52) U.S. Cl. ............... 606/79; 606/86 A; 606/86 R
(58) Field of Classification Search ............. 606/79–85, 606/86 R, 99, 86 A
See application file for complete search history.

(56) References Cited

U.S. PATENT DOCUMENTS

| | | | |
|---|---|---|---|
| 4,239,045 | A | 12/1980 | Schlein |
| 4,827,928 | A | 5/1989 | Collis, Jr. |
| 4,881,534 | A | 11/1989 | Uhl et al. |
| 5,135,528 | A | 8/1992 | Winston |
| 5,167,725 | A | 12/1992 | Clark et al. |
| 5,314,477 | A | 5/1994 | Marnay |
| 5,423,825 | A | 6/1995 | Levine |
| 5,562,736 | A | 10/1996 | Ray et al. |
| 6,261,293 | B1 | 7/2001 | Nicholson et al. |
| 6,261,295 | B1 | 7/2001 | Nicholson et al. |
| 6,413,278 | B1 | 7/2002 | Marchosky |
| 6,485,495 | B1 | 11/2002 | Jenkinson |
| 6,517,544 | B1 | 2/2003 | Michelson |
| 6,599,291 | B1 | 7/2003 | Foley et al. |
| 6,610,089 | B1 | 8/2003 | Liu et al. |
| 6,641,582 | B1 | 11/2003 | Hanson et al. |
| 6,648,895 | B2 | 11/2003 | Burkus et al. |
| 6,679,886 | B2 | 1/2004 | Weikel et al. |
| 2002/0138145 | A1 | 9/2002 | Marchosky |
| 2003/0023306 | A1 | 1/2003 | Liu et al. |
| 2003/0028197 | A1 | 2/2003 | Hanson et al. |
| 2003/0139812 | A1 | 7/2003 | Garcia et al. |
| 2003/0171814 | A1 | 9/2003 | Muhanna et al. |
| 2003/0176867 | A1 | 9/2003 | Long et al. |
| 2003/0187448 | A1 | 10/2003 | Michelson |
| 2003/0195517 | A1 | 10/2003 | Michelson |
| 2003/0195520 | A1 | 10/2003 | Boyd et al. |
| 2003/0195629 | A1 | 10/2003 | Pafford et al. |
| 2003/0212404 | A1 | 11/2003 | Dorchak |
| 2004/0215198 | A1* | 10/2004 | Marnay et al. ............... 606/86 |

FOREIGN PATENT DOCUMENTS

| | | |
|---|---|---|
| WO | WO-01/01893 | 1/2001 |
| WO | WO-01/19295 | 3/2001 |

\* cited by examiner

*Primary Examiner*—Thomas C Barrett
*Assistant Examiner*—Michael J Araj
(74) *Attorney, Agent, or Firm*—Woodcock Washburn LLP

(57) ABSTRACT

An instrument, instrument system and method for cutting a cutout in a vertebral bone adjacent an intervertebral space are provided which make use of a cutting blade. The cutting blade is mounted on a support structure for movement toward and cutting into the vertebral bone. A stop arrangement is also mounted on the support structure and is movable relative to the cutting blade to a position to limit movement of the cutting blade into the vertebral bone. Typically, the limited movement cutting is made after two cutouts are provided in adjacent vertebral bones using a trial implant.

21 Claims, 3 Drawing Sheets

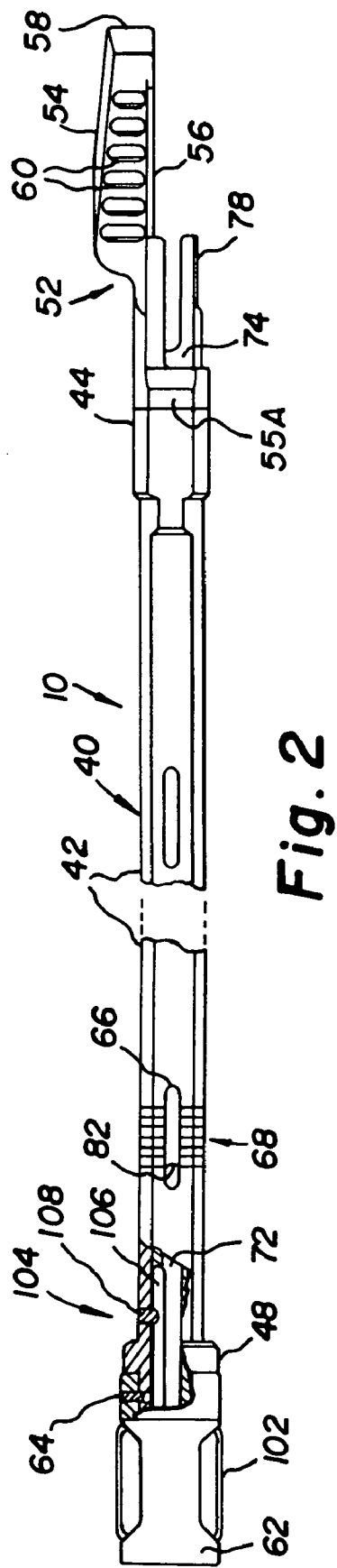
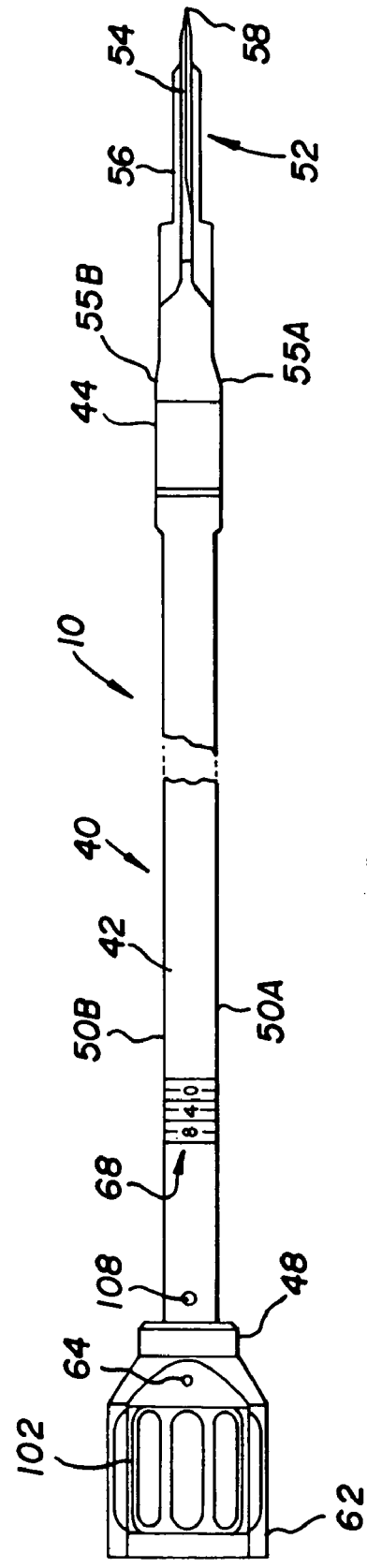
Fig. 2
Fig. 3

ADJUSTABLE CUTTING OF CUTOUT IN VERTEBRAL BONE

BACKGROUND OF THE INVENTION

This invention relates to intervertebral implants; and more specifically, it relates to new and improved instruments and methods for preparing an intervertebral space for receiving an artificial intervertebral disc implant (sometimes referred to below simply as an implant).

When it is necessary to completely remove a disc from between adjacent vertebrae, the conventional procedure is to fuse the adjacent vertebrae together. More recently, there have been important developments in the field of disc replacement, namely disc arthroplasty. Disc arthroplasty involves the insertion of an artificial intervertebral disc implant into the intervertebral space between adjacent vertebrae, thereby allowing limited universal movement of the adjacent vertebrae with respect to each other.

Some instruments have been developed to date for preparing an intervertebral space for receiving an artificial disc implant. These instruments include a set of different sizes of trial implants, different ones of which are inserted into a cleaned out intervertebral space until the correct size trial implant has been determined, thereby determining the size of the actual implant to be inserted. The trial implant may have a fixed stop member in the form of a pin fixed to the rear end of the trial implant and extending vertically for engaging the vertebrae to limit movement of the trial implant into the intervertebral space. Some implants have a raised keel which requires that a cutout or slot be formed in the vertebrae adjacent the intervertebral space for receiving these raised keels. One known arrangement for forming these cutouts is a chisel which can be mounted with chisel portions movable along guiding slots in the top and bottom of the selected trial implant as the chisel portions cut into the adjacent vertebrae to form the two cutouts.

One known artificial disc implant is shown in Published application No. WO 01/01893, published Jan. 11, 2001, and instruments for inserting same are shown in Published application No. WO 01/19295, published Mar. 22, 2001. Another disclosure of artificial disc implants and apparatus associated therewith is contained in U.S. Ser. No. 10/423,879 filed Apr. 28, 2003. The teachings of these three references are hereby incorporated by reference.

While these known instruments and methods represent a substantial improvement in the art, there exists a continuing need for improvements in the field of instruments and methods for preparing an intervertebral space for receiving an artificial intervertebral disc implant.

BRIEF SUMMARY OF THE INVENTION

A purpose of the present invention is to provide new and improved instruments and related methods for preparing an intervertebral space for receiving an artificial intervertebral disc implant, particularly where a cutting tool has been used in conjunction with a trial implant to provide first and second opposed (paired) cutouts in the vertebrae located on opposite sides of a trial implant. When such paired cutouts are prepared, they are usually substantially identical in both width, height, and depth (length). However, in some situations, it may be desired for one cutout to have a different depth than the other cutout.

The instrument of the present invention may be used to prepare the intervertebral space at any location along the spine, including especially the lumbar and cervical spines. However, since the cervical vertebrae are so small relative to the lumbar vertebrae, i.e., about 20% of the area of the lumbar spine vertebrae, some instruments may be more suited than others for the cervical spine.

While the trial implant as well as the intervertebral implant is normally inserted from the patient's anterior moving towards the patient's posterior, it is to be understood that the implant, the instruments and the method can also be designed and arranged to insert the implant laterally or obliquely, i.e., from the side, in which case the keels thereof will be oriented on the implant for such lateral movement and the cutouts in the adjacent vertebrae will be opened toward a lateral side to receive the keels. To avoid confusion with respect to the patient's anatomy, the invention will be described herein with respect to more simple terminology which relates to the instruments and methods themselves. For example, in describing the invention, the terms "front" or "forward" mean the part of the instrument which faces toward the vertebrae or is moving in the direction of movement toward the vertebrae, while the words "back", "rear" or "rearward" refer to the end of the instrument farthest from the vertebrae or moving away from the vertebrae. Also, in this application, the words "upper" or "lower" or "uppermost" or "lowermost" or any other words describing the orientation of the intervertebral implant or the instruments or methods associated therewith are used only for convenience of description and are not intended to convey any limitation. More specifically, the parts of the implant, the instruments and/or the methods described in this application with reference to the upper part can in fact be positioned as the superior or inferior part within the patient's vertebrae, with the other of the two parts being the opposite part.

It is thus an object of the present invention to provide new and improved instruments for preparing an intervertebral space for receiving an artificial intervertebral disc implant.

The instruments and the methods of the present invention are particularly adapted for the ultimate implantation of an artificial intervertebral disc implant having upper and lower parts which undergo limited universal movement with respect to each other, with the upper and lower surfaces of the upper and lower parts engaging the adjacent vertebral surfaces as well known in the art. These instruments and methods of the present invention are particularly for use where the implant has a keel extending from the vertebrae engaging surfaces into slots or cutouts formed in the adjacent vertebrae.

In accordance with a first aspect of the present invention, there is provided an instrument, instrument system and method for cutting a slot or cutout in a vertebral bone, or for lengthening an already formed cutout.

In accordance with an illustrative embodiment of the present invention, an instrument or instrument system for further cutting an already formed cutout, or even for initially cutting a cutout, into a first vertebral bone located adjacent a trial implant is provided. A trial implant is located in an intervertebral space between the first vertebral bone and a second vertebral bone, which trial implant has a holding device for holding the trial implant in the intervertebral space. The holding device includes a shaft which engages the trial implant and which extends rearwardly therefrom. Then a cutting instrument is provided in accordance with the present invention which has a cutting tool for creating or lengthening one cutout. This cutting instrument also includes a stop which limits forward movement of the cutting tool. The position of this stop is adjustable, to adjust the depth of cut of the cutting tool, and hence the length or increased length of the cutout.

In accordance with the present invention, a method for increasing by a predetermined distance a depth of a first cutout cut into a first vertebral bone located adjacent a trial implant is disclosed. In this method, a first cutout is initially cut in the first vertebral bone and a second cutout in the second vertebral bone. This is accomplished using a first cutting tool with first and second chisel portions which cut the first and second cutouts simultaneously. Then, after removing the first cutting tool from the shaft, a second cutting tool is placed on the shaft. This second cutting tool has a single chisel portion which is received all of the way into the first cutout (the cutout to be extended). An adjustable stop on the second cutting tool is then or previously adjusted to have a predetermined offset distance away from an adjacent surface of the trial implant (or in other words, away from the tip of the chisel portion), with this predetermined offset distance being equal to the predetermined distance of depth increase desired. The second cutting tool is then advanced forward until the adjustable stop contacts the adjacent surface of the trial implant, which forward advancement effects a cutting of the vertebral bone and hence an increase in depth of the first cutout by the predetermined distance. After that, the second cutting tool is removed from the shaft.

Thus, it is an object of the present invention to provide new and improved instruments for preparing an intervertebral space for receiving an artificial disc implant, particularly where a first cutout for receiving a keel of the artificial disc implant must be longer than a second cutout for the opposite keel of the artificial disc implant.

It is another object of the present invention to provide new and improved methods for preparing an intervertebral space for receiving an artificial disc implant, particularly where a first cutout for receiving a keel of the artificial disc implant must be longer than a second cutout for the opposite keel of the artificial disc implant.

These and other objects of the present invention will be apparent from the detailed description to follow, together with the accompanying drawings.

BRIEF DESCRIPTION OF THE SEVERAL VIEWS OF THE DRAWINGS

Preferred embodiments of the invention will now be described by way of example with reference to the accompanying drawings, wherein:

FIG. 2 is a left side view of the cutting instrument depicted in FIG. 1;

FIG. 3 is a top view of the cutting instrument depicted in FIG. 1;

DETAILED DESCRIPTION OF THE INVENTION

Initially, it will be noted that the instruments and methods described herein are applicable for preparing an intervertebral space for subsequent insertion of a wide range of artificial disc implants. And while the instruments and methods described herein include the concept of forming cutouts to receive raised keels, it will be appreciated that these instruments and methods are adaptable for preparing a space where any artificial implant having such keels is used.

Figure 4:
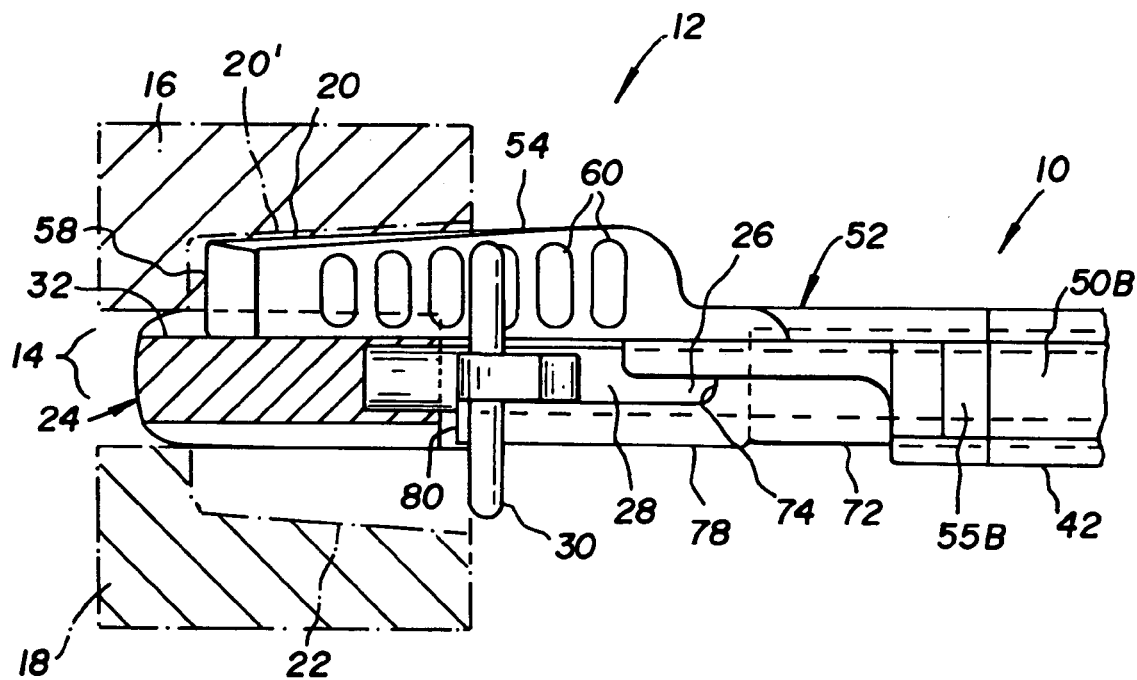
FIG. 4 is a right side view of the cutting portion of the cutting instrument depicted in FIG. 1 together with a schematic cross-sectional depiction of a trial implant located between adjacent vertebral bones.

With reference now to the drawings in which like numerals represent like elements throughout the views, a presently preferred instrument 10 in accordance with the present is depicted in FIGS. 1-4. As best shown in FIG. 4, instrument 10 is part of an instrument system 12, where instrument system 12 is typically used for finishing the preparation of an intervertebral space 14 located between a first vertebral bone 16 and a second vertebral bone 18. The initial preparation of intervertebral space 14 is performed with any of many instruments known in the art, with the preparation typically ending where a two pronged chisel instrument produces two identical cutouts 20 and 22 in vertebral bones 16 and 18 with the guidance of a trial implant 24. It will be appreciated that cutout 20 is identical with the side profile of the chisel part of instrument 10 received therein and thus cutout 20 is shown in FIG. 4 without separation from the chisel part. It will also be appreciated that instrument 10 can be used to initially provide a single cutout in either vertebral bone 16 or 18 if desired, and then to provide the other cutout with a different depth if desired and in a manner which will be evident subsequently.

Figure 5:
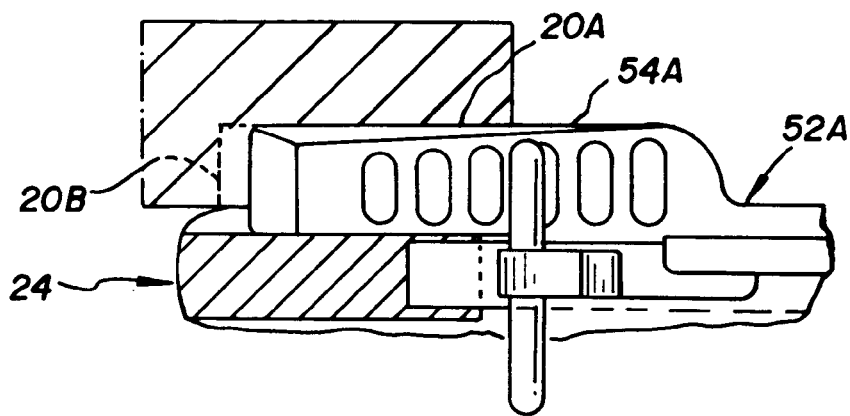
FIG. 5 is a right side view of the cutting portion of an alternative cutting instrument from that depicted in FIG. 1 together with a schematic cross-sectional depiction of a top part of a trial implant and an adjacent vertebral bone.

As an alternative-to the angled (relative to the guiding surface of implant 24) cutout 20 depicted in FIG. 4, and perhaps more typically as depicted in FIG. 5, the initial cutout 20A (and similar cutout on the opposite side not depicted) can be parallel to implant 24. In this case, it is only the overall length of cutout 20A, and not the height as well as in the embodiment of FIG. 4, which is extended by instrument 10 to, for example, the length of cutout 24B as schematically depicted. If desired, of course, the chisel as depicted in FIG. 4 could be used with cutout 20A, to increase both the length of cutout 20A as well as the height.

As also known in the art, trial implant 24 includes a holding device 26 having a shaft 28 which is brazed (or alternatively, threadably received) onto trial implant 24 and which extends rearwardly therefrom. Holding device 26 is used to insert trial implant 24 into a cleaned intervertebral space 14 up to the position where an implant stop 30 attached to one lateral side of trail implant 24 contacts bones 16 and 18 as shown. Conveniently, shaft 28 has a handle 29 on the distal end to facilitate insertion of trial implant 24 into place, which handle is then removed from shaft 28 so as not to interfere with the remaining procedures involving trial implant 24 (as described below). Implant stop 30 thus acts to properly place trail implant 24 in intervertebral space 14, and to maintain trial implant 24 at this position when identical cutouts 20 and 22 are cut by the two pronged chisel instrument as it moves forward along shaft 28 as well appreciated by those of ordinary skill. Located along a top side (and typically-along the bottom side as well where the two pronged chisel instrument is used) of trial implant 24 is a groove 32 in which the mating chisel part of instrument 10 is slidably guided during cutting of bone 16 as the chisel instrument is advanced along shaft 28.

Figure 1:
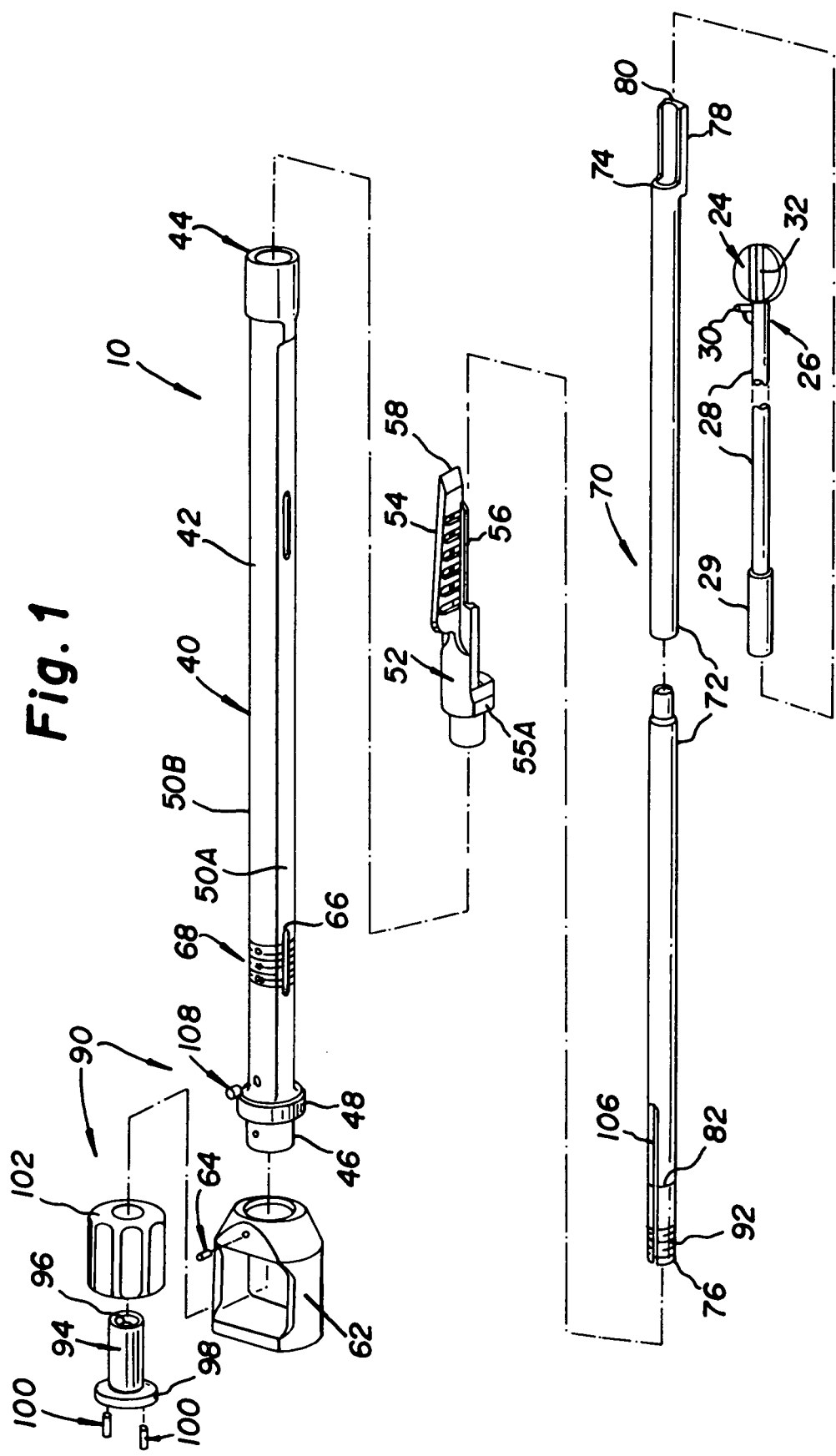
FIG. 1 is an exploded front, top, and left side perspective view of a cutting instrument of the present invention.

As shown best in FIGS. 1-3, instrument 10 of the present invention includes a cutting tool 40 having an elongate cutting shank 42. Cutting shank 42 includes a front end 44 and a rear end 46 at which a lateral extending flange 48 is located. Cutting shank 42 is preferably a hollow generically cylindrical tube. From flange 48 forward, cutting shank 42 is provided with flats 50A and 50B on opposite lateral sides from one another as shown. By use of flats 50A and 50B, a similarly shaped slotted (U-shaped) hammer (not shown, but as known in the art) can be easily positioned around cutting shank 42 to provide an axially rearward impact against flange 48 to move cutting tool 40 backwards and away from vertebral bones 16 and 18 if desired. It will be appreciated that flats 50A and 50B can be omitted (so that cutting shank 42 is circular throughout its length) if the slot of the hammer is larger than the diameter of cutting shank 42.

Provided at front end 44 of cutting shank 42 is a chisel 52 which is attached to cutting shank 42 by silver soldering or the like of the mating surfaces. Chisel 52 includes a blade portion 54 located to be extending forward from an upper portion of front end 44. As best shown in FIG. 1, chisel.52 includes flats 55A and 55B which are matingly aligned with flats 50A and 50B of cutting shank 42 so that the axial (or frontal) profile of cutting shank 42 including flats 50A and 50B is about the same as that of chisel 52 including flats 55A and 55B. It will be appreciated that chisel 52 is configured so that chisel 52 does not extend vertically into a bottom half of the axial profile of cutting shank 42 (that is, chisel 52 is located within the top half of the axial profile of cutting shank 42); and so that chisel 52 does not extend laterally beyond the cross sectional profile of cutting shank 42.

Chisel 52 has a lower guiding section 56 which is received in groove 32 for guided sliding movement along the top of trial implant 24, in the same manner as noted above for the prior art two pronged chisel instrument. Blade portion 54 of chisel 42 includes a tip 58 and holes or fenestrations 60 therealong in which bits of cut bone or the like can gather so as not to interfere with the cutting action of blade portion 54 as cutting shank 42 is moved in a cutting motion from front to back (as discussed subsequently). With this configuration at front end 44 of cutting shank 42, front end 44 including chisel 52 easily fits past stop 30 of trial implant 24 (no matter whether chisel 52 is up or down).

Provided at a rear end 46 of cutting shank 42 is an impact portion formed as a cage 62. Cage 62 is securely attached to rear end 46 via a pin 64 which is snugly received in mating holes in cage 62 and rear end 46 as shown. When cage 62 is secured to rear end 46, the front portion of cage 62 is engaged with flange 48 so that the rear portion of cage 62 serves as a relatively flat impact surface against which a suitable hammer or the like can be struck to impart a forward movement to cutting shank 42 and hence to chisel 52 to cut vertebral bone 16.

Located along flat 50A of cutting shank 42, but close to rear end 46, is a window slot 66 which extends to the interior hollow portion of cutting shank 42. Circumferentially about cutting shank 42 at the location of window slot 66 is a reference scale 68. Scale 68 is formed by a series of concentric and equally spaced marks or cuts about cutting shank 42, conveniently spaced in millimeter increments or the like as desired.

Cutting instrument 10 also includes a stop 70 which serves to limit a forward movement of cutting tool 40 during cutting with chisel 52. Stop 70 includes a stop shank 72 having a front end 74 and a rear end 76. Stop shank 72 is preferably a hollow generally cylindrical tube which is internally sized to be slidably received on shaft 28 of holding device 26 with little play so that sliding movement of stop shank 72 relative to shaft 28 is smooth and precise. In addition, the outside diameter or dimensions of stop shank 72 are sized so that cutting shank 42 is slidably received on stop shank 72 with little play so that a sliding movement of cutting shank 42 relative to stop shank 72 is smooth and precise and hence there is a sliding movement of cutting shank 42 relative to shaft 28 as well. As shown, stop shank 72 is conveniently formed of two pieces silver soldered together at their mating surfaces.

As shown best in FIG. 1, front end 74 includes a stop member 78 which is shaped to extend forward from a lower portion of front end 74 and which terminates with a stop surface 80. Stop member 78 has a vertical profile which fits within the profile of chisel 52 which is immediately thereabove, so that like chisel 52, stop member 78 can also move past stop 30 of trial implant 24. As explained subsequently, as stop member 78 moves past stop 30, stop surface 80 engages or presses against trial implant 24 as shown in FIG. 4. While stop member 78 has been shown with the particular flattened shape in order to move past stop 30, stop member 78 could just continue the cylindrical shape of stop shank 72 if this were to necessary. Stop 70 also includes a reference mark 82 on the outer surface of stop shank 72 adjacent to rear end 76. Reference mark 82 is positioned and designed to be viewable through window slot 66 of cutting shank 42 and is used in conjunction with reference scale 68 adjacent window slot 66 in a manner to be described subsequently.

Cutting tool 10 further includes an adjustment mechanism 90 which is used to adjustably connect stop member 78 relative to cutting tool 40, whereby a longitudinal position of stop member 78 relative to tip 58 of chisel 52 is likewise adjustable. Thus, by proper adjustment, when stop surface 80 of stop member 78 engages trial implant 24, tip 58 can be determined to have cut into bone 16 by a predetermined and desired distance. It will be appreciated that reference mark 82 as seen through window slot 66 and relative to reference scale 68 can be used in determining the predetermined distance and length of cut as will be discussed subsequently.

In this preferred embodiment, adjustment mechanism 90 includes a threaded interconnection between cutting shank 42 and stop shank 72 so that relative rotation of one threaded connection with respect to the other causes cutting shank 42 to move relative to stop shank 72. In particular, stop shank 72 includes external/male threads 92 at rear end 76 thereof, while cutting shank 42 includes a reaction bolt 94 having internal/female threads 96 which are matingly received by threads 92. In order to achieve relative movement of threads 92 and 96, reaction bolt 94 includes a head 98 which rotatably abuts against the adjacent inside end of the opening of cage 62. In addition, reaction bolt 96 is pressed into an outer shell or rotation member 102 and then reaction bolt 96 is positively prevented from rotation by securing pins 100 which pass into outer shell 102. Shell 102 extends radially out beyond cage 62 so that reaction bolt 96 is easily rotated within cage 62 by engagement with shell 102. It will be appreciated that the position of the male and female threads could be reversed and the operation would be the same.

In order to prevent stop shank 72 from rotating together with shell 102 and reaction bolt 96, and in order to align cutting shank 42 circumferentially relative to stop shank 72 and hence to keep stop 70 properly aligned in use, adjustment mechanism 90 also includes an aligning means 104. Aligning means 104 includes an axial slot 106 provided adjacent rear end 76 of stop shank 72 (or elsewhere along stop shank 72 if desired) together with a pin 108 which is secured in cutting shank 42 and which is slidably received in axial slot 106. It will thus be appreciated that by rotation of shell 102 (and hence rotation of male threads 96), the axial position of stop shank 72, and hence the axial position of stop surface 80, is adjusted relative to cutting shank 42 and hence relative to tip 58 of chisel 52.

In operation, instrument 10 has the following method of use and instrument system 12 functions in the following manner. Initially, after intervertebral space 14 is suitably prepared (as well known in the art), trial implant 24 is inserted therein. Trial implant 24 is properly positioned by holding device 26, especially by the manipulation of shaft 28 extending rearwardly therefrom and which is accessible by the user. Typically, a two-pronged or dual chisel cutting chisel device (not shown) is selected by the user according to a predetermined desired length of cut into vertebral bones 16 and 18.

This dual chisel device is positioned by the user on shaft 28, and moved forward onto trial implant 24 with corresponding guiding portions of each chisel portion located in a corresponding guiding groove 32 of trial implant 24. As the dual chisel device is moved (by impacts) from front to back, two opposite cutouts are made in the adjacent vertebral bones 16 and 18. The dual chisel device has a central bridging portion between the chisel portions so that the cutting of the cutouts continues until the central portion of the dual chisel device engages trial implant 24, at which time two opposite and desired length cuts 20 and 22 are made in vertebral bones 16 and 18 as shown in FIG. 4. The dual chisel device is then removed from about shaft 28, typically followed by a subsequent implanting of the permanent and corresponding sized artificial implant.

While the above procedure has been satisfactory in most situations, in certain situations such as where there is a large lordosis angle or retrolisthesis, one of the cutouts formed by the dual chisel may be too short (not deep enough for the keel of the permanent implant). In such a situation, extension of only one cutout is needed, which is here depicted as the top cutout 20 in FIG. 4 or top cutout 20A in FIG. 5. Thus, cutting instrument 10 is used to extend top cutout 20 by an amount which is predetermined by fluoroscopy or the like prior to cutting with instrument 10.

To determine the extra length needed for cutout 20, it would be possible to view cutout 20 while the dual chisel device is in place and to then determine that cutout 20 needs to be extended by, for example, 2 mm. Alternatively, it would be possible to view cutout 20 after removal of the dual chisel to make this determination. Thus, with instrument 10 located in other than a cutting position (either outside of the body of the patient or positioned on shaft 28 away from vertebral bone 16), stop surface 80 can be adjusted using shell 102 and reference mark 82 so that it is further by 2 mm from tip 58 than the central bridging portion of the dual chisel was from the corresponding tip (that is, the depth of cut of the dual chisel plus the predetermined distance). Such an adjustment of stop surface 80 can also be accomplished with reference to the dual chisel itself (or rather the top chisel part thereof and the bridge). Thus, where the dual chisel is used as a guide for the length of cut already made, direct comparison or measurement is made of the tip to bridge portion distance. Reference mark 82 and reference scale 68 can also be used to precisely adjust the extra length of cut if desired rather than relying on additional measurements.

Alternatively and preferably when usable, instrument 10 is moved along shaft 28 until blade portion 54 is all of the way in top cutout 20, and the user can then decide using an active fluoroscopy how much further cutout 20 should be extended (e.g., 2 mm). Then, stop surface 80 is correspondingly adjusted using shell 102, with attention to reference mark 82 and reference scale 68 if desired. Of course, the user can simply look at blade portion 54 in place using the active fluoroscopy and then back stop surface 80 away from trial implant 24 (and hence away from chisel tip 58) by an amount which looks sufficient (e.g., about 2 mm).

Once stop surface 80 is positioned as desired and instrument 10 is in place, the impact surface of cage 62 is impacted by a suitable hammer or the like to move cutting shank 42 forward to cut vertebral bone 16 until stop surface 80 engages trial implant 24. At this time, further advance of chisel 52 is not possible, and hence chisel 52 has been driven forward a sufficient amount to effect the predetermined extension of cutout 20, such as shown by extended cutout 20' shown in FIG. 4 by a chained line.

As noted above, in the more typical case, it will only be desired to extend the depth of cut of the cutout provided by the dual chisel and this is shown in FIG. 5. Thus, blade portion 54A of chisel 52A is used in the same manner as described above for chisel 52 to extend the depth of cut of cutout 20A to cutout 20B. However, as the top of blade portion 54A is parallel to implant 24, no additional height is cut, only the additional length is cut when instrument 10 is used therewith.

While the present invention has been described above primarily with an application to extending the length of a cutout which had already been cut together with a similar cutout on the opposite vertebral bone, it will be appreciated that instrument 10 can also be used with a trial implant to make an initial cutout of a predetermined length on one side of the trial implant in one vertebral bone, and then by reversing the position of instrument 10, instrument 10 can make a second cutout of a different or same predetermined length in the opposite vertebral bone.

It will also be appreciated that if desired a suitable ball plunger or other tactile or auditory mechanism could be used in conjunction with cage 62 to provide an indication to the user every time that cage 62 is turned a certain amount, such as a tenth of a millimeter. This would make it easier to judge how far cage 62 should be rotated to move stop surface 80 of stop member 78 as desired.

It will further be appreciated that the location of stop shank 72 inside of cutting shank 42 and about shaft 28 could be reversed, so that cutting shank 42 is located inside of stop shank 72 and about shaft 28.

Although the invention has been described in considerable detail with respect to preferred embodiments thereof, it will be apparent that the invention is capable of numerous modifications and variations, apparent to those skilled in the art.

What is claimed is:

1. An instrument system for preparing a first vertebral bone adjacent an intervertebral space, the intervertebral space positioned between the first vertebral bone and a second vertebral bone, the instrument system comprising:
   a trial implant;
   a holding device including a holding shaft, the trial implant securable to the holding shaft;
   a cutting tool including a cutting shank and a chisel mounted to a front end of the cutting shank, the holding shaft slidably positionable within the cutting shank; and
   a stop including a stop shank, a stop member and a stop surface, the holding shaft slidably received in the stop shank, and the stop shank slidably received in the cutting shank, wherein the stop member limits forward motion of the chisel relative to the trial implant.

2. The instrument system as recited in claim 1, further comprising:
   an implant stop attached to a lateral side of the trial implant, the implant stop contacting the first and second vertebral bones in a contacting position; and
   an adjustment mechanism that adjusts a position of the stop member relative to the cutting tool.

3. The instrument system as recited in claim 2, wherein the chisel includes a tip, a distance between the stop surface and the tip adjustable by manipulating the adjustment mechanism.

4. The instrument system as recited in claim 2, wherein the stop member abuts the trial implant when the trial implant is disposed in the intervertebral space in the contacting position so as to determine a depth of a cutout in the first vertebral bone.

5. The instrument system as recited in claim 2, wherein the adjustment mechanism comprises a knob that is rotatable to adjust the position of the stop member relative to the cutting tool.

6. The instrument system as recited in claim 1, further comprising:
a window slot; and
a reference scale disposed adjacent the window slot that indicates a position of the stop member relative to the cutting tool.

7. The instrument system as recited in claim 6, further comprising:
a reference mark located on the stop member that is visible through the window slot in an assembled configuration.

8. The instrument system as recited in claim 7, wherein the stop member includes a stop shank, the cutting shank receives the stop shank and the stop shank receives the holding shaft in the assembled configuration.

9. The instrument system as recited in claim 1, further comprising:
a cage including an impact surface, the cage attached to a rear end of the cutting shank opposite the cutting tool, the impact surface being relatively flat.

10. The instrument system as recited in claim 9, further comprising:
an adjustment member including a rotation member coupled to the rear end such that rotation of the rotation member imparts relative rotation between the cutting tool and the stop shank to adjust the position of the stop member relative to the cutting tool.

11. The instrument system as recited in claim 1, wherein the stop is threadably connected to the cutting tool.

12. The instrument system as recited in claim 1, wherein the chisel includes a guiding section that guides the cutting tool into the intervertebral space.

13. The instrument system as recited in claim 12, wherein trial implant includes a guiding groove, the guiding section receivable in the guiding groove.

14. The instrument system as recited in claim 1, wherein the chisel is two pronged.

15. An instrument system for creating a cutout in a vertebral bone, wherein the vertebral bone partially defines an intervertebral space, the instrument comprising:
a cutting tool including a cutting shank that defines a forward end and rearward end, and a chisel disposed at the forward end of the cutting shank, the chisel having a guiding section, the chisel configured to create the cutout in the vertebral bone as the cutting tool moves forward toward the vertebral bone;
a trial implant including a guiding groove, the guiding section slidably received in the guiding groove when the trial implant is disposed in the intervertebral space to guide the chisel into the vertebral bone along a desired direction; and
a stop supported by the cutting shank, wherein the stop has an adjustable position relative to the chisel, and the stop includes a stop member that is configured limit forward movement of the cutting tool to a depth in the vertebral bone that is dependent upon the position of the stop relative to the chisel.

16. The instrument system as recited in claim 15, wherein the stop is received inside the cutting shank.

17. The instrument system as recited in claim 15, wherein the stop member abuts the trial implant in a contacting position.

18. The instrument system as recited in claim 16, wherein the stop further includes a stop shank, the stop shank being movable relative to the cutting tool.

19. The instrument system as recited in claim 16, further comprising:
a holding device including a holding shaft, the holding device movably attached to the stop and the cutting tool, the holding shaft configured to attach to the trial implant at an implant connection end.

20. The instrument system as recited in claim 19, wherein the holding device further includes an implant stop disposed adjacent the implant connection end, the implant stop abuts the vertebral bone to determine an insertion depth of the trial implant into the intervertebral space.

21. The instrument system as recited in claim 15, further comprising:
a window slot in the cutting shank and reference scale disposed adjacent the window slot that indicates a position of the stop member relative to the cutting tool.

* * * * *

UNITED STATES PATENT AND TRADEMARK OFFICE
CERTIFICATE OF CORRECTION

| | | |
|---|---|---|
| PATENT NO. | : 7,763,024 B2 | Page 1 of 1 |
| APPLICATION NO. | : 10/947661 | |
| DATED | : July 27, 2010 | |
| INVENTOR(S) | : Rudi Bertagnoli et al. | |

It is certified that error appears in the above-identified patent and that said Letters Patent is hereby corrected as shown below:

Column 4,
Line 23, delete "alternative-to" and insert -- alternative to --.
Line 40, delete "trail" and insert -- trial --.
Line 45, delete "trail" and insert -- trial --.
Line 50, delete "typically-along" and insert -- typically along --.

Column 5,
Line 8, delete "chisel.52" and insert -- chisel 52 --.

Column 6,
Line 8, after "were to" insert -- be --.

Signed and Sealed this

Twelfth Day of October, 2010

David J. Kappos
*Director of the United States Patent and Trademark Office*